United States Patent [19]

Crivello et al.

[11] 4,374,066
[45] Feb. 15, 1983

[54] METHOD FOR MAKING TRIARYLSULFONIUM SALTS

[75] Inventors: James V. Crivello, Clifton Park; Julia L. Lee, Schenectady, both of N.Y.

[73] Assignee: General Electric Company, Schenectady, N.Y.

[21] Appl. No.: 200,769

[22] Filed: Oct. 27, 1980

Related U.S. Application Data

[63] Continuation-in-part of Ser. No. 79,692, Sep. 28, 1979.

[51] Int. Cl.³ .......................... C07F 9/68; C07F 9/90; C07F 5/02
[52] U.S. Cl. ................................. 260/440; 260/446; 568/6; 568/13
[58] Field of Search .................... 260/446, 440; 568/6, 568/13

[56] References Cited

U.S. PATENT DOCUMENTS 2,807,648 9/1957 Pitt ........................................ 568/74
4,161,478 7/1979 Crivello .......................... 260/441 X
4,173,476 11/1979 Smith et al. ........................... 568/74
4,196,138 4/1980 Cella ................................ 260/441 X
4,197,174 4/1980 Chang ............................. 260/441 X
4,247,472 1/1981 Watt ..................................... 260/440
4,247,473 1/1981 Chang .................................. 260/440

OTHER PUBLICATIONS

Complex Triarylsulfonium Salt Photoinitiators. I. The Identification, Characterization, and Syntheses of a New Class of Triarylsulfonium Salt Photoinitiators, Crivello et al., J. of Poly. Sci.: Poly Chem. Ed., vol. 18, 2677–2695 (1980).

Primary Examiner—Helen M. S. Sneed
Attorney, Agent, or Firm—William A. Teoli; James C. Davis, Jr.; James Magee, Jr.

[57] ABSTRACT

A method for making triarylsulfonium salts is provided based on the reaction of an aromatic hydrocarbon, a sulfur chloride, and chlorine in the presence of a Friedel Crafts catalyst. The triarylsulfonium salts can be used as cationic photoinitiators to effect the deep section cure of a variety of organic resin compositions.

5 Claims, No Drawings

METHOD FOR MAKING TRIARYLSULFONIUM SALTS

CROSS REFERENCE TO RELATED APPLICATIONS

This application is a continuation-in-part of copending application Ser. No. 079,692, filed Sept. 28, 1979. Cross reference is made to our copending application Ser. No. 046,116, filed June 16, 1979 and assigned to the same assignee as the present invention.

BACKGROUND OF THE INVENTION

The present invention relates to certain triarylsulfonium salts having chemically combined sulfur or oxygen containing monovalent polyaryl radicals and photocurable compositions containing such triarylsulfonium salts.

Prior to the present invention, as shown by Crivello U.S. Pat. Nos. 4,058,401, 4,069,055 and 4,161,478, epoxy resins and other cationically polymerizable organic materials were rapidly cured under ultraviolet light with various aryl sulfonium salts, where all of the aforementioned patents are assigned to the same assignee as the present invention. Although valuable results were achieved by the use of such photocurable compositions and photoinitiators, the cure of the cationically polymerizable organic material was generally effective to a thickness of up to about 10–15 mils to a tack-free state within a period of up to about 60 seconds. Experience has shown that in certain applications, for example, encapsulation of electronic components, protective coatings, etc., and the like, deep section curing of various cationically polymerizable organic material, that is a cure of at least 20 mils, is often required. As a result, the use of the triarylsulfonium salt photoinitiators has been somewhat restricted.

STATEMENT OF THE INVENTION

The present invention is based on the discovery that photoinitiators having the formula, $$[(R)_a(R^1)_b(R^2)_cS]^+[Y]^-, \quad (1)$$

have been found effective for the deep section cure of a wide variety of cationically polymerizable organic materials, such as epoxy resins, phenol formaldehyde resins, vinyl ethers, episulfides, cyclic amines, etc., under either ultraviolet light, or visible light when used in combination with certain organic sensitizers, as described hereinafter, where R in formula (1), is a monovalent organic radical having the formula, $$R^3\mathord{+}X\mathord{+}R^4\!\!-\!\!\!\underset{(Z)_d}{\diagdown}\!\!,$$

$R^1$ is a monovalent $C_{(6-13)}$ aromatic organic radical, $R^2$ is a divalent $C_{(6-20)}$ aromatic radical forming a heterocyclic or fused ring structure, $R^3$ is a mono or divalent $C_{(6-13)}$ aromatic radical, $R^4$ is a divalent or trivalent $C_{(6-13)}$ aromatic radical, X is —S—,

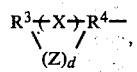

or —O—, Y is a non-nucleophilic anion defined more particularly below, Z is a divalent radical selected from

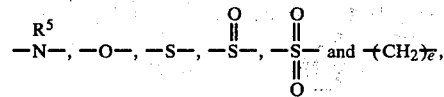

and $R^5$ is a $C_{(1-13)}$ organic radical, a is an integer equal to 1 to 3 inclusive, b is a whole number equal to 0 to 2 inclusive, c is a whole number equal to 0 or 1, and the sum of a+b+c is equal to 3, d is a whole number equal to 0 or 1, and e is an integer equal to 1 to 4 inclusive. In addition, it has been found that the cure of the aforementioned cationically polymerizable organic materials is substantially faster when utilizing the photoinitiators of formula (1) as compared to the photoinitiators of the prior art.

Some of the non-nucleophilic anions shown by Y of formula (1) are, for example, $MQ_n$, where M is a metal or metalloid, Q is a halogen radical and n has a value of 4–6 inclusive, where $MQ_n$ is preferably $MF_6$, such as $PF_6^-$, $SbF_6^-$, $AsF_6^-$ and $SbF_5OH^-$. In addition, Y also can include perchlorate, $CF_3SO_3^-$, $C_6H_4SO_3^-$, $Cl^-$, $Br^-$, $F^-$, $I^-$, nitrate, phosphate, $CF_3CO_2^-$, $F_2PO_2^-$, etc.

There is provided by the present invention photocurable compositions comprising (A) a cationically polymerizable organic material and (B) an effective amount of photoinitiator of formula (1).

Radicals included by R of formula (1) are, for example,

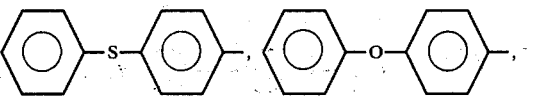

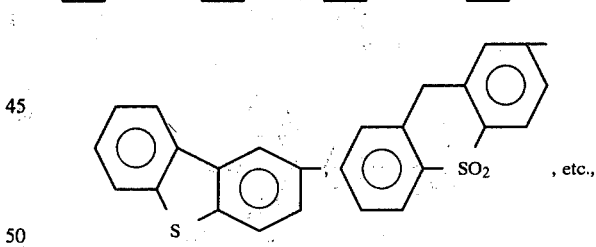
, etc., derivatives of such radicals, substituted with 1–4, $C_{(1-8)}$ alkyl, or alkoxy radicals, such as the corresponding methyl, methoxy, ethyl, propyl, butoxy, etc., halogen radicals, for example, chlorine, bromine or fluorine, etc. Radicals included within $R^1$ are more particularly phenyl, tolyl, xylyl, naphthyl, anthryl. Radicals included by $R^2$ are, for example,

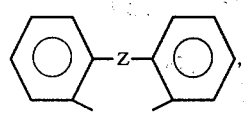

where Z is as previously defined.

Included by the triarylsulfonium salts of formula (1), are compounds having the formula,

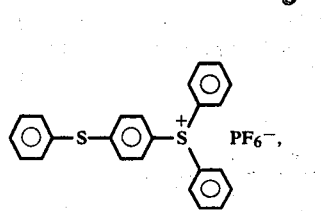

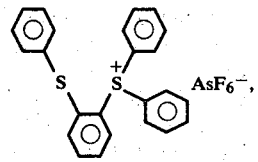

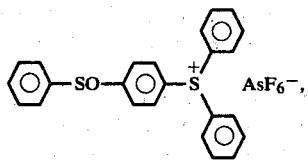

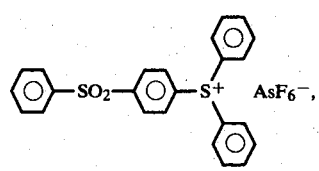

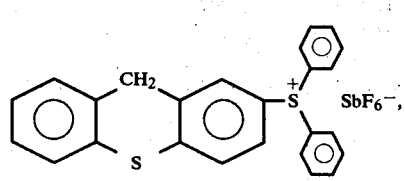

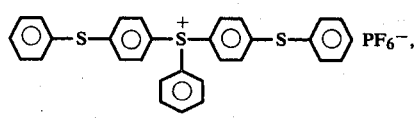

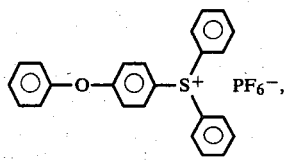

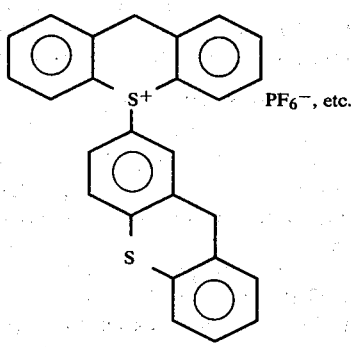

The triarylsulfonium salts of formula (1) can be made by procedures related to methods shown in our copending application Ser. No. 046,115, filed June 6, 1979 and assigned to the same assignee as the present invention. A diarylthioether can be reacted with a diaryliodonium salt in the presence of a copper (II) catalyst as shown by the following

where R, $R^1$, M, Q and n are as previously defined. An additional method is based on the use of $AlCl_3$. In U.S. Pat. No. 2,807,648, H. M. Pitt shows a direct Friedel Crafts condensation of an aromatic hydrocarbon using $AlCl_3$. A method which can be used to make some of the photoinitiators of formula (1) is based on the use of sulfur monochloride and chlorine as follows:

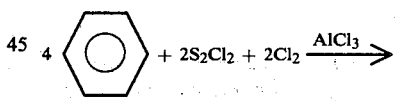

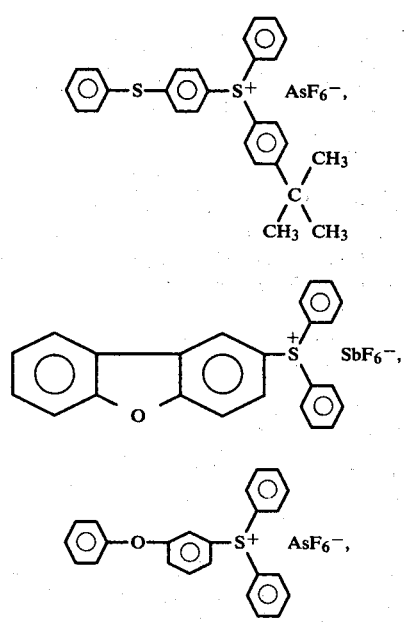

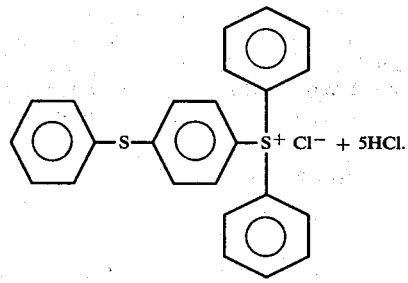

The above triarylsulfonium salt can be converted to the preferred photoinitiators of formula (1), where Y is $MQ_n$ or $MF_6$ by a metathesis using alkali metal $MQ_n$ or $MF_6$ salts such as $KMQ_n$, $KMF_6$, $NaMF_6$, etc.

Organic polymerizable materials which can be utilized in the photocurable compositions of the present invention include epoxy resins such as monomeric, dimeric or oligomeric or polymeric epoxy materials containing one or a plurality of epoxy functional groups. For example, those resins which result from the reaction of bisphenol-A (4,4'-isopropylidenediphenol) and epichlorohydrin, or by the reaction of low molecular weight phenolformaldehyde resin (Novolak resin) with epichlorohydrin, can be used alone or in combination with an epoxy containing compound as a reactive diluent. Such diluents as phenyl glycidyl ether, 4-vinylcyclohexene dioxide, limonene dioxide, 1,2-cyclohexene oxide, glycidyl acrylate, glycidyl methacrylate, styrene oxide, allyl glycidyl ether, etc., may be added as viscosity modifying agents.

In addition, the range of these compounds can be extended to include polymeric materials containing terminal or pendant epoxy groups. Examples of these compounds are vinyl copolymers containing glycidyl acrylate or methacrylate as one of the comonomers. Other classes of epoxy containing polymers amenable to cure using the above catalysts are epoxysiloxane resins, epoxy-polyurethanes and epoxy-polyesters. Such polymers usually have epoxy functional groups at the ends of their chains. Epoxysiloxane resins and method for making are more particularly shown by E. P. Plueddemann and G. Ganger, J. Am. Chem. Soc. 80 632–5 (1959). As described in the literature, epoxy resins can also be modified in a number of standard ways such as reaction with amines, carboxylic acids, thiols, phenols, alcohols, etc., as shown in U.S. Pat. Nos. 2,935,488; 3,235,620; 3,369,055; 3,379,653; 3,398,211; 3,403,199; 3,563,840; 3,567,797; 3,677,995; etc. Further coreactants which can be used with epoxy resins are hydroxy terminated flexibilizers such as hydroxy terminated polyesters, shown in the Encyclopedia of Polymer Science and Technology, Vol. 6, 1967, Interscience Publishers, New York, pp. 209–271 and particularly p. 238.

Included by the thermosetting organic condensation resins of formaldehyde which can be used in the practice of the present invention are, for example, urea type resins, phenol-formaldehyde type resins, etc.

In addition, there can be used melamine thiourea resins, melamine, or urea aldehyde resins, cresol-formaldehyde resins and combinations with other carboxy, hydroxyl, amino and mercapto containing resins, such as polyesters, alkyds and polysulfides.

Some of the vinyl organic prepolymers which can be used to make the polymerizable compositions of the present invention are, for example, $CH_2=CH-O-(CH_2-CH_2O)_{n'}-CH=CH_2$, where $n'$ is a positive integer having a value up to about 1000 or higher, multi-functional vinylethers, such as 1,2,3-propane trivinylether, trimethylolpropane trivinylether, prepolymers having the formula,

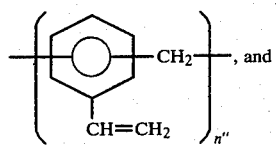

low molecular weight polybutadiene having a viscosity of from 200 to 10,000 centipoises at 25° C., etc. Products resulting from the cure of such compositions can be used as printing inks and other applications typical of thermosetting resins.

A further category of the organic materials which can be used to make the polymerizable compositions are cyclic ethers which are convertible to thermoplastics. Included by such cyclic ethers are, for example, oxetanes such as 3,3-bis-chloromethyloxetane, alkoxyoxetanes as shown by Schroeter U.S. Pat. No. 3,673,216, assigned to the same assignee as the present invention; oxolanes such as tetrahydrofuran, oxepanes, oxygen containing spiro compounds, trioxane, dioxolane, etc.

In addition to cyclic ethers, there are also included cyclic esters such as β-lactones, for example, propiolactone, cyclic amines, such as 1,3,3-trimethyl-azetidine and organosilicon cyclics, for example, materials included by the formula,

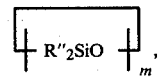

where $R''$ can be the same or different monovalent organic radical such as methyl or phenyl and m is an integer equal to 3 to 8 inclusive. An example of an organosilicone cyclic is hexamethyl trisiloxane, octamethyl tetrasiloxane, etc. The products made in accordance with the present invention are high molecular weight oils and gums.

The photocurable compositions of the present invention can be made by blending the cationically polymerizable organic material with an effective amount such as from 0.1% to 15% by weight of the photocurable composition of the triarylsulfonium salt of the formula (1).

In certain instances, an organic solvent, such as acetone, nitromethane and acetonitrile can be used to facilitate the mixing of various ingredients. The triarylsulfonium salts can be formed in situ if desired. In addition, the curable compositions may contain inactive ingredients, such as silica, talc, clay, glass fibers, extenders, hydrated alumina, carbon fibers, process aids, etc., in amounts of up to 500 parts of filler per 100 parts of cationically polymerizable organic material. The curable compositions can be applied to such substrates as metal, rubber, plastic, molded parts of films, paper, wood, glass, cloth, concrete, ceramic, etc.

Some of the applications in which the curable compositions of the present invention can be used are, for example, protective, decorative and insulating coatings, potting compounds, printing inks, sealants, adhesives, molding compounds, wire insulation, textile coatings, laminates, impregnated tapes, varnishes, etc.

In order that those skilled in the art will be better able to practice the invention, the following examples are given by way of illustration and not by way of limitation. All parts are by weight.

EXAMPLE 1

A mixture of 19.6 parts of 86% potassium hydroxide, 33 parts of thiophenol and about 120 parts of dimethylacetamide was heated at a temperature of 120° C. with stirring to effect the removal of water. After about 6.5 parts of water was collected, there was added to the resulting mixture 26.3 parts of para-dibromobenzene and the mixture was heated to reflux. After 6 hours at reflux the reaction mixture was allowed to cool and 300 parts of water was added. There was obtained a tan colored solid which was filtered and washed with water several times. The product was then dried. There was obtained 34.7 parts of 1,4-dithiophenoxybenzene based on method of preparation.

A mixture of 7.35 parts of the above disulfide, 11.75 parts of diphenyliodonium hexafluoroarsenate and 0.2 part of copper benzoate was heated for 3 hours at 120° C. The resulting reaction mixture was washed several times with about 50 part portions of diethylether and the remaining solid was recrystallized from 95% ethanol. There was obtained a 45% yield of a very light tan crystalline product having a melting point of 69°–75° and the following elemental analysis: Calculated %C, 51.3; %H, 3.50; %S, 11.43. Found %C, 51.21; %H, 3.59; %S, 11.37. Based on method of preparation there was obtained a triarylsulfonium salt having the formula,

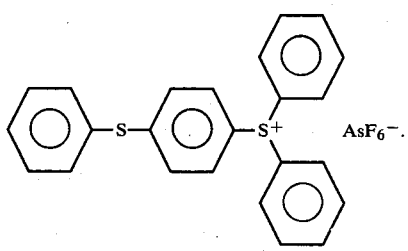

A 3% solution of the above photoinitiator was prepared in 4-vinylcyclohexene dioxide. A similar solution was prepared for triphenylsulfonium hexafluoroarsenate. The respective solutions were then measured for tack-free time using a GE H3T7 mercury arc lamp at a distance of 6 inches from the substrate which consisted of the respective epoxy formulas applied as a 1 mil film onto a glass slide. The photoinitiator of the present invention had a tack-free time of less than 1 second while the triphenylsulfonium hexafluoroarsenate mixture had a tack-free time of about 5 seconds.

EXAMPLE 2

Chlorine was introduced into a mixture of 37.2 parts of diphenylsulfide and 13.34 parts of aluminum chloride to a total of 9.5 parts of chlorine was added with stirring. The reaction mixture was poured onto 500 parts of ice to effect the decomposition of the aluminum chloride complex. There was obtained a white semi-solid which was washed twice with 200 part portions of hot water. There was then added to the resulting washed residue, 27.8 parts of potassium hexafluoroarsenate and 500 parts of hot water and the mixture was stirred at a temperature of 30° C. for 1 hour. There was obtained an orange oil which separated and which was recovered by decanting the aqueous solution. It was purified by washing with water several times and finally with anhydrous ethyl ether. The resulting product was then dried under reduced pressure at 60° C. for 16 hours. The product was then recrystallized from 95% ethanol. There was obtained a 31% yield of a triarylsulfonium salt having a melting point of 77°–87° C. Based on method of preparation, the salt had the following formula:

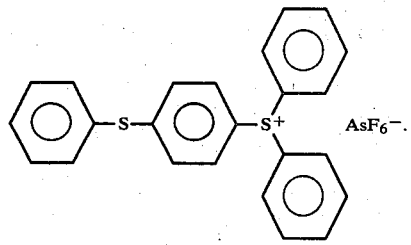

EXAMPLE 3

Three percent solutions were prepared consisting of 3,4-epoxycyclohexylmethyl-3',4'-epoxycyclohexanecarboxylate and triphenylsulfonium hexafluoroarsenate (Prior art) and the photoinitiator of the present invention as shown by Example 2. Films of increasing thickness were drawn onto glass plates and cured for one minute using a G.E. H3T7 medium pressure mercury arc lamp at a distance of 6 inches from the films. The thickest film which could be cured down to the glass to a non-tacky state using the aforementioned photoinitiators is shown as follows:

| Photoinitiator | Max. Thickness |
| --- | --- |
| Prior Art | 10–15 mils |
| Example 2 | 50 mils |

The above results show that the photocurable compositions of the present invention containing a photoinitiator within the scope of formula (1) cured to a thickness more than 4 times that of the photocurable composition of the prior art.

EXAMPLE 4

Additional photocurable compositions were prepared utilizing the photoinitiators of Example 2 and cyclohexene oxide as a cationically polymerizable organic material. The solution contained 0.021 mols of photoinitiator per liter of cyclohexene oxide. Aliquots of these photocurable mixtures (3 ml) were irradiated under sealed conditions using a Hanovia 450 medium pressure mercury arc lamp. The aliquots were withdrawn periodically, quenched at various times and the polymer isolated by precipitation in methanol. The resulting photocured products were recovered by filtering and drying the polymer overnight at 60° C. in vacuo. The polymer was weighed to determine the percent conversion. The following table shows the results obtained, where the values are expressed in percent conversion:

TABLE II

| Irradiation Time | Photoinit. (prior art) | Photoinit. (Example 2) |
| --- | --- | --- |
| 0.5 | 8 | 32 |
| 1 min. | 14 | 41 |
| 2 min. | 18 | 49 |
| 4 min. | 34 | 64 |
| 6 min. | 49 | 69 |
| 8 min. | 55 | 77 |

EXAMPLE 5

The procedure of example 4 was repeated except that in place of the cyclohexene oxide there was utilized 2-chloroethylvinylether. Four ml aliquots of the mixture were irradiated in accordance with the procedure of Example 4 to provide the following percent conversion values:

TABLE III

| Irradiation Time | Photoinit. (prior art) | Photoinit. (Example 2) |
| --- | --- | --- |
| 15 sec. | 0 | 17 |
| 30 sec. | 0 | 43 |
| 60 sec. | 0 | 87 |
| 300 sec. | 0 | 87 |
| 2100 sec. | 2 | 87 |

The above results show that the photoinitiators of the present invention are superior to the photoinitiator of the prior art.

EXAMPLE 6

The procedure of Example 4 was repeated except that in the place of the cyclohexene oxide there was utilized trioxane and methylene chloride. Solutions were prepared containing $1.386 \times 10^{-1}$ mol of trioxane and $1.386 \times 10^{-4}$ mol of photoinitiator. The mixtures were then irradiated in accordance with the procedure of Example 5 resulting in the following percent conversion values.

TABLE IV

| Irradiation Time | Photoinit. (prior art) | Photoinit. (Example 2) |
| --- | --- | --- |
| 30 sec. | 0 | 9 |
| 60 sec. | 0 | 86 |
| 120 sec. | 0 | 78 |
| 240 sec. | 60 | 85 |

EXAMPLE 7

One percent solutions were prepared consisting of diethyleneglycol divinyl ether and triphenylsulfonium hexafluoroarsenate and the photoinitiator of the present invention as shown by Example 2. Ten grams of each of the above mixtures were poured into identical 2 in. diameter cups and irradiated for 5 seconds at a distance of 23 cm from a GE H3T7 medium pressure mercury arc lamp. The solid polymer was removed from the cups, washed with acetone to remove unreacted divinyl ether and then dried. The respective weights of the dry polymers were proportional to the thickness of cure in the samples.

| Photoinitiator | Weight (grams) |
| --- | --- |
| Prior Art | 0.89 |
| Example 2 | 2.33 |

The above results show that the photocurable compositions of the present invention containing a photoinitiator within the scope of formula (1) cured to a thickness of more than 2.6 times that of the prior art. On a molar basis, the compounds of the present invention were 3.2 times more efficient than the prior art.

EXAMPLE 8

Two percent solutions were prepared consisting of Methylon 75201, a phenol-formaldehyde resole of the formula,

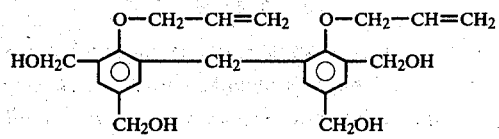

and triphenylsulfonium hexafluoroarsenate (prior art) and the photoinitiator of the present invention as shown by Example 2. The two solutions were spread as 3 mil films onto glass plates and exposed to UV light at a distance of 6 inches from a GE H3T7 mercury arc lamp. The resin film containing the photoinitiator of the present invention required 1.5 minutes to become tack-free whereas the film containing the photoinitiator of the prior art required 5.5 minutes irradiation under the same conditions.

EXAMPLE 9

The previous example was repeated except the phenol-formaldehyde was replaced with a silicone resin having the following formula,

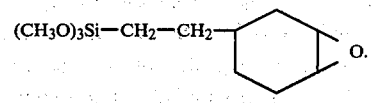

After 10 seconds irradiation, the sample containing the photoinitiator of Example 2 was tack-free and could not be removed by rubbing with acetone. On the other hand, the sample containing the triphenylsulfonium salt was soft and readily removed by acetone.

EXAMPLE 10

The above example was repeated in which the resin employed had the following molecular structure: (A-187 Union Carbide Corp.)

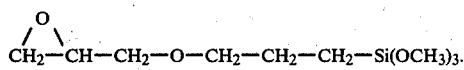

Seventy-five seconds irradiation were necessary to produce a tack-free 3 mil film using the photoinitiator of the prior art, while only 30 seconds were required to give a tack-free film with the photoinitiator of the present invention.

EXAMPLE 11

Three percent solutions in cycloaliphatic epoxy resin ERL 4221 of photoinitiators of the formulas,

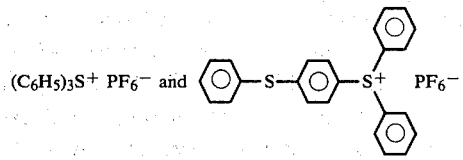

were applied onto glass substrates and cured in accordance with Example 7. After washing the resulting cured films with acetone and allowing them to dry the films were weighed. The photoinitiator of the present invention was found to provide a film twice as thick as that of the prior art.

EXAMPLE 12

A three percent solution of the photoinitiator of Example 2 in 3,4-epoxycyclohexylmethyl-3',4'-epoxycyclohexane carboxylate was prepared. The sample was divided into equal portions and 0.5% by weight perylene was added to one of the solutions. The samples were exposed to visible light from a GE H3T7 lamp fitted with a filter to remove all ultraviolet light at wavelengths below 390 nm. The sample containing the perylene dye sensitizer cured within 30 seconds, while the sample free of dye remained uncured even after 5 minutes irradiation. This example demonstrates the use of dye sensitizers in combination with the photoinitiators of the present invention to provide visible light curable compositions.

EXAMPLE 13

A mixture was stirred for 18 hours at room temperature consisting of 11.2 parts (0.02 mole) of diphenyl-4-thiophenoxyphenyl sulfonium hexafluoroarsenate, 20 parts of glacial acetic acid, and about 4 parts of 30% hydrogen peroxide. The mixture was then poured into 200 parts of distilled water. A crude product was obtained which was washed with water and then with anhydrous ethyl ether. Based on elemental analysis, spectroscopic analysis and method of preparation, the product had the following structure:

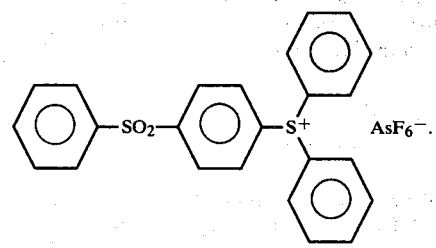

A three percent solution of the above photoinitiator in 4-vinylcyclohexene dioxide cured to a tack-free film when irradiated with a GE H3T7 lamp at a distance of 10 inches.

EXAMPLE 14

There was added 11.2 parts (0.02 mole) of the sulfonium salt of Example 2 in about 15 parts of acetone. There was then added, 2 parts of 30% hydrogen peroxide, slowly with cooling. The solution was allowed to stir overnight and then poured into 200 parts of water. An oil was obtained which solidified on washing with water followed by anhydrous ethyl ether. The product which was obtained after drying overnight in vacuo had a melting point of 70°-74° F. and by elemental analysis, and spectroscopic analysis as well as by method of preparation had the following structure:

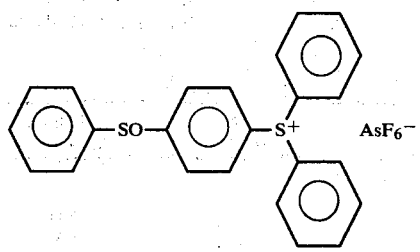

A three percent solution of the above photoinitiator in 4-vinylcyclohexene dioxide cured as a film as described in the previous example had a tack-free time of 2 seconds.

EXAMPLE 15

A mixture of 160 parts of benzene and 43 parts of anhydrous aluminum chloride was stirred and 67 parts of sulfur monochloride were slowly added. The reaction mixture was maintained at a temperature of between 30°-35° C. During the addition, the reaction mixture became dark orange in color. After the addition was completed, 60 parts of chlorine gas was introduced slowly into the reaction mixture and the resulting mixture became dark purple and slightly viscous. The mixture was then poured into 500 parts of ice water to decompose the aluminum chloride complex. There was obtained an off-white semi-solid. The solid was then washed twice with hot water. There was then added 500 parts of water and the resulting suspension was heated to 80° C. There was then added 92 parts of potassium hexafluoroarsenate which was filtered into the hot aqueous sulfonium chloride syspension. The mixture was then allowed to stir for 1 hour. There was obtained a yellow, thick oil which was separated and dried in a vacuum oven at 60° C. Based on method of preparation, a 85% yield of the triarylsulfonium salt of Example 1 was obtained.

A 3% solution of the above photoinitiator was prepared in 3,4-epoxycyclohexylmethyl-3',4'-epoxycyclohexane carboxylate. The mixture was spread as a 1 mil film and irradiated as described in Example 1 to give a tack-free time of 5 seconds.

In a further aspect of the present invention, there is provided a method for making triarylsulfonium salts of the formula,

which comprises (1) effecting reaction between a $C_{(6-13)}$ aromatic hydrocarbon, sulfur monochloride, or sulfur dichloride and chlorine in the presence of a Friedel Crafts catalyst, (2) contacting the resulting reaction mixture with water to decompose the resulting complex, (3) effecting a metathesis with the resulting triarylsulfonium chloride and an alkali metal $MQ_n$ salt and (4) recovering the resulting triarylsulfonium salt from the mixture, where $R^1$ is a $C_{(6-13)}$ monovalent aromatic hydrocarbon radical, $R^6$ is a divalent $C_{(6-13)}$ aromatic hydrocarbon radical, M is a metal or metalloid, Q is a halogen radical and n has a value of 4–6 inclusive.

In the above-described method for making triarylsulfonium salts of formula (2) there can be utilized from 4 to 6 moles of aromatic hydrocarbon per mole of sulfur monochloride, $S_2Cl_2$, or from about 8 to 12 moles of aromatic hydrocarbon, per mole of sulfur dichloride, $SCl_2$. Reaction can be effected at from $-10°$ C. to $100°$ C. There also can be used 2 to 10 moles of chlorine per mole of aromatic hydrocarbon. The Friedel Crafts catalyst can be used at from 0.1% to 100% by weight, based on the weight of reaction mixture. Suitable Friedel Crafts catalysts are, in addition to aluminum chloride, $AlBr_3$, $SnCl_4$, $PF_5$, $BF_3$, $AsF_5$, $SbF_5$, $TaF_5$, $BCl_3$, etc. As previously indicated, the above sulfonium chloride of formula (2) can be converted to the triarylsulfonium salts of formula (1) by a metathesis reaction using an alkali metal $MF_6$ salt, such as $KPF_6$. Some of the aromatic hydrocarbons which can be utilized in the method for making the triarylsulfonium salts of formula (2) are benzene, toluene, xylene, etc. In addition, depending upon the reactants utilized, substantially inert organic solvents also can be used to facilitate reaction. Suitable organic solvents are, for example, $CH_2Cl_2$, $CS_2$, $CH_3NO_2$, $CCl_4$,

etc.

Although the above examples are directed to only a few of the very many variables which can be used in the practice of the present invention, it should be understood that the present invention is broadly directed to UV curable compositions, certain triarylsulfonium salts included within formula (1) and methods for making such materials. As utilized in the definition of the present invention, the expression "effective amount" when applied to the triarylsulfonium salt is that amount required for cure of the organic material. It has been found 0.1% to 15% by weight of the triarylsulfonium salt, based on the weight of photocurable composition can be used.

What we claim as new and desire to secure by Letters Patent of the United States is:

1. A method for making triarylsulfonium salts of the formula,

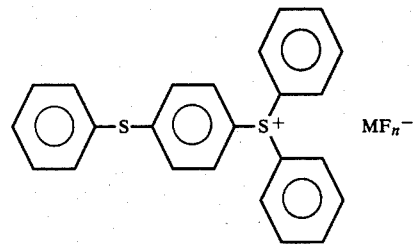

which comprises,
(1) stirring a mixture of 4 moles of benzene per mole of sulfur monochloride in the presence of an effective amount of aluminum chloride at a temperature of between about 30°–35° C.,
(2) introducing chlorine into the mixture in an amount substantially equivalent to the moles of sulfur monochloride utilized in (1),
(3) combining the mixture of (2) with sufficient water to decompose the resulting complex,
(4) recovering the resulting triphenylsulfonium chloride from the mixture of (3),
(5) combining the recovered triphenylsulfonium chloride in the form of an aqueous mixture with an alkali metal or metalloid salt selected from the class consisting of potassium hexafluoroarsenate, potassium hexafluoroantimonate and sodium tetrafluoroborate and
(6) recovering the resulting triphenylsulfonium polyfluoro metal or metalloid salt from the mixture of (5), where M is a metal or metalloid selected from arsenic, antimony and boron, and n is an integer having a value of 4–6.

2. A method in accordance with claim 1, which comprises effecting reaction between benzene, sulfur monochloride, and chlorine in the presence of aluminum chloride.

3. A method in accordance with claim 1, utilizing potassium hexafluoroarsenate.

4. A method in accordance with claim 1, utilizing potassium hexafluoroantimonate.

5. A method in accordance with claim 1, utilizing sodium tetrafluoroborate.

* * * * *